United States Patent
Tokita (10) Patent No.: US 7,444,866 B2
(45) Date of Patent: Nov. 4, 2008

(54) SYSTEM FOR REHABILITATION TRAINING USING MUSCLE FORCE DATA MEASURED OF A PERSON BOTH BEFORE IMPAIRED AND WHEN IMPAIRED

(75) Inventor: Mamoru Tokita, Gunma (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 0 days.

(21) Appl. No.: 11/889,520

(22) Filed: Aug. 14, 2007

(65) Prior Publication Data
US 2008/0041153 A1 Feb. 21, 2008

(30) Foreign Application Priority Data
Aug. 21, 2006 (JP) .............................. 2006-224240

(51) Int. Cl.
*A61B 5/22* (2006.01)
(52) U.S. Cl. .................................................. 73/379.01
(58) Field of Classification Search ............. 73/379.01, 73/397.02; 345/156; 600/595; 463/36
See application file for complete search history.

(56) References Cited

U.S. PATENT DOCUMENTS 5,429,140 A * 7/1995 Burdea et al. ............... 600/587

2002/0143277 A1 * 10/2002 Wood et al. ................. 600/595
2006/0217233 A1 * 9/2006 Lee .................................. 482/9
2006/0290663 A1 * 12/2006 Mitchell ....................... 345/156
2007/0282228 A1 * 12/2007 Einav et al. .................... 601/33

FOREIGN PATENT DOCUMENTS

JP 2002-191718 7/2002
JP 2007-061137 3/2007

* cited by examiner

*Primary Examiner*—Jewel Thompson
(74) *Attorney, Agent, or Firm*—Venable LLP; Michael A. Sartori; Catherine M. Voorhees (57) ABSTRACT

A system for rehabilitation training is able to specify the muscle of a person in need of rehabilitation, and also to help the person to set a proper goal of training. To this end, the system includes a trainer device for measuring living data of the person and for training him or her, and a data server for keeping the living body data of the person measured by the trainer device. The system further includes a menu formulator. When the person is to undergo the process of rehabilitation, the menu formulator compares his or her living body data measured by the trainer device to his or her living body data measured when he or she was not impaired and kept in the data server to find out a difference therebetween. A menu for rehabilitation is formed based on the difference, so that rehabilitation effects will be enhanced.

6 Claims, 7 Drawing Sheets

SYSTEM FOR REHABILITATION TRAINING USING MUSCLE FORCE DATA MEASURED OF A PERSON BOTH BEFORE IMPAIRED AND WHEN IMPAIRED

BACKGROUND OF THE INVENTION

1. Field of the Invention

The present invention relates to a system for rehabilitation training.

2. Description of the Background Art

In general, a person has, when impaired on his or her body or under medical care for prolonged time, due to an accident or a disease, his or her muscular force weakened significantly. Hence, such a person usually undergoes the process of rehabilitation training to develop his or her muscular force for the sake of leading a normal life. It is desirable in such a case to prepare a menu for rehabilitation suited to each individual and to carry out the process of rehabilitation training in accordance with the so prepared menu.

There has been proposed a system wherein, at the beginning of rehabilitation training, a physical measurement is carried out to obtain living body data of a patient to be trained so as to prepare a suitable menu for rehabilitation for the patient based on the living body data. See for example, Japanese patent laid-open publication No. 2002-191718.

In the above conventional system, a manager for rehabilitation prepares an exercise prescription program for the patient based on the living body data measured at the beginning of the rehabilitation training in order to execute for the patient the menu for rehabilitation in accordance with the exercise prescription program. Moreover, the living data of the patient may be transmitted over a communication network, and he or she may therefore undergo the process of rehabilitation anywhere.

However, in the conventional system, the exercise prescription program is prepared based on living body data measured at a time when the patient who needs rehabilitation undergoes the initial process of the rehabilitation. This means that the exercise prescription program cannot be prepared based on living body data measured at a time when the patient was in fine fettle. Therefore, the conventional system cannot provide for the patient the menu for rehabilitation best suited to achieving the objective for leading a normal life.

SUMMARY OF THE INVENTION

It is an object of the present invention to provide a system for rehabilitation training which is free from the above problem and with which it is possible to improve the effect of rehabilitation.

It is a more specific object of the present invention to provide a system for rehabilitation training in which it is possible to determine the muscle of a person in need of training and to set an optimum goal for training in order to enhance the effect of rehabilitation.

In accordance with the present invention, a system for rehabilitation training is provided in which the living body data of a person when rehabilitation was not necessary were measured and are held to be compared to the living body data of the same person when rehabilitation has become necessary to produce difference data therebetween, which are used to prepare a menu for rehabilitation for that person.

In accordance with the present invention, there is provided a system for rehabilitation training which includes a trainer device for measuring living data of a person and for training the person, and a data server for storing the living body data of the person measured by the trainer device. The system further includes a menu formulator for forming a menu for rehabilitation. The menu formulator compares the living body data measured of the person, when undergoing the process of rehabilitation, by the trainer device to the living body data which was measured of the person, when not impaired, and is stored in the data server, to find out a difference between both of the living body data, thereby forming the menu based on the difference.

According to one aspect of the present invention, the living body data is of the force of muscles, and the menu formulator forms the menu with the muscle of which muscular force is weakened specified.

According to another aspect of the present invention, the trainer device includes a bi-articular arm device having a structure simulating an upper limb or a lower limb of a human being. The bi-articular arm device measures the muscular force of the person and performs training for his or her upper or lower limb.

In a system for rehabilitation training, according to the present invention, living body data of a person before rehabilitation has become necessary are measured and kept, and the living body data so kept are compared to the living body data of the same person when rehabilitation has become necessary. Based on difference data resultant from the comparison, a menu for rehabilitation is prepared. By so doing, the muscles in need of training of a person to be rehabilitated, or rehabilitant, may be optimally specified, while a goal for training may optimally be set, thereby enhancing the effect of rehabilitation.

BRIEF DESCRIPTION OF THE DRAWINGS

The objects and features of the present invention will become more apparent from consideration of the following detailed description taken in conjunction with the accompanying drawings in which.

DESCRIPTION OF THE PREFERRED EMBODIMENT

Figure 1:
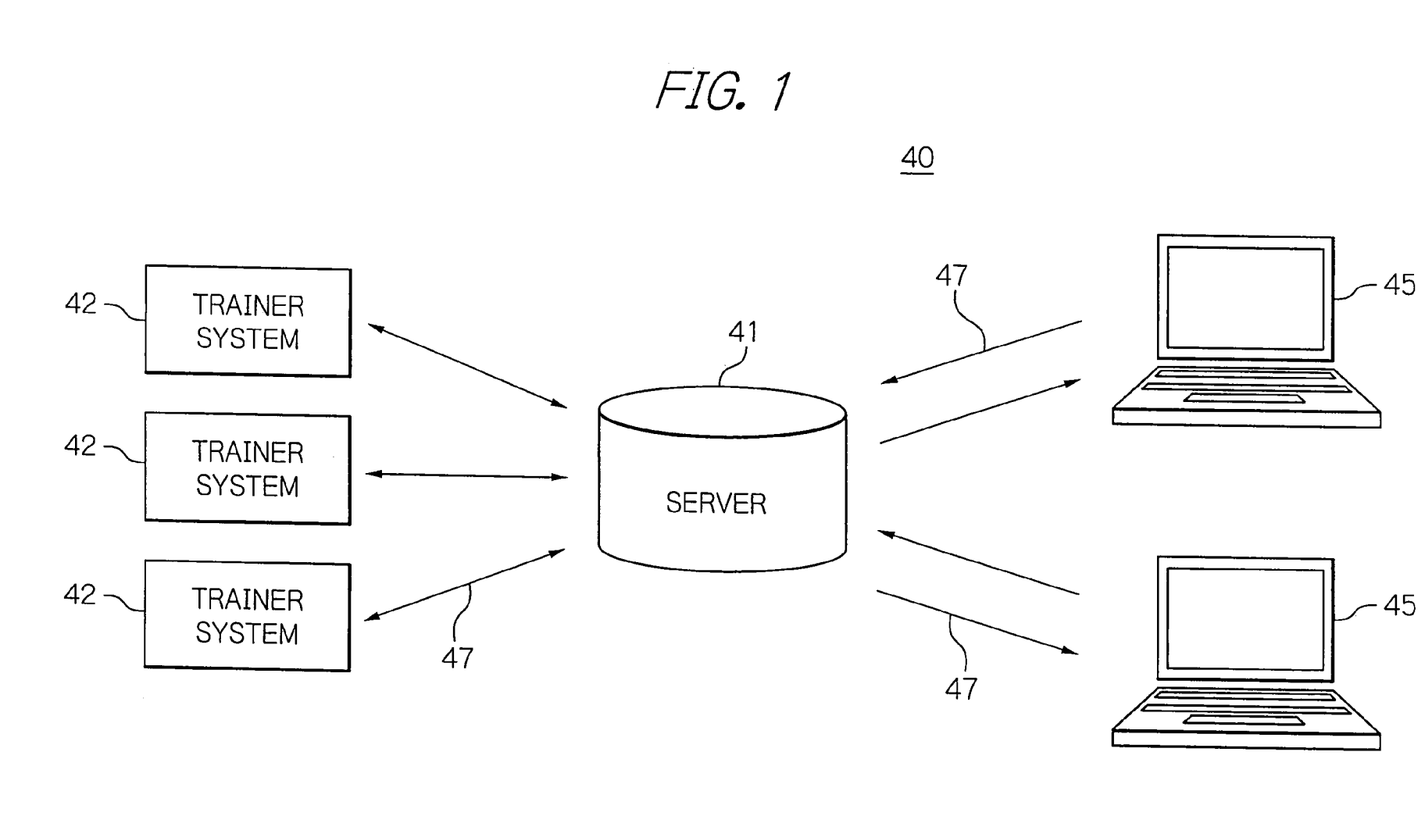
FIG. 1 schematically shows a preferred embodiment of a system for rehabilitation training according to the present invention.
Figure 2:
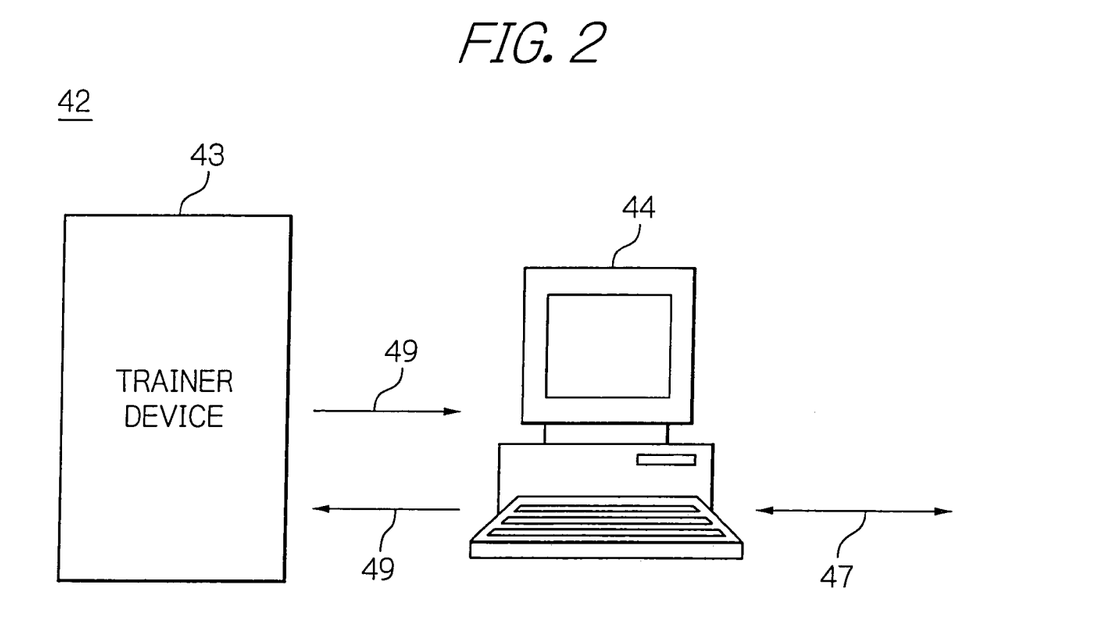
FIG. 2 schematically shows a preferred embodiment of the trainer system shown in FIG. 1.

A preferred embodiment of a system for rehabilitation training in accordance with the present invention will be described reference to the accompanying drawings. FIG. 1 shows the constitution of a system for rehabilitation training according to a preferred embodiment of the present invention. FIG. 2 shows the constitution of a trainer system according to the preferred embodiment.

Referring first to FIG. 1, a system 40 for rehabilitation training, embodying the present invention, is adapted to measure the muscular force, as living body data, of a person to be rehabilitated, or rehabilitant, 60, only partly depicted in FIGS. 6 and 7 as later described, to store the so measured value or values of the muscular force of the rehabilitant 60, and compare the data of the muscular force thus stored to the newly measured data of the muscular force to prepare a menu, or schedule, for rehabilitation training of the rehabilitant 60, in accordance with which menu training of the muscular force of the rehabilitant for rehabilitation will be performed.

The rehabilitant 60 may, for example, be a person who has his or her force of muscles degraded due to some cause, such as aging, who has his or her body impaired by an accident or disease, or who has been under medical care for prolonged time due to physical injury or disease, and who tries to undergo the process of rehabilitation to recover his or her muscular force. However, the rehabilitant 60 may be other than the above persons. The system 40 for rehabilitation training may be used for measuring such a person beforehand, that is, before he or she needs rehabilitation, his or her force of muscles, and hold, or store, the thus measured data of the muscular force therein. Later on, when such a person wishes to get the process of rehabilitation required, the system 40 is again used to measure his or her force of muscles and compare the thus newly obtained data with the data kept therein to prepare a menu, or schedule, for rehabilitation for that person. In line with the menu, or schedule, for rehabilitation thus prepared, the system 40 is used to train or rehabilitate his or her muscular force of the rehabilitant 60 in the course of rehabilitation training.

The system 40 includes trainer systems 42, a system server 41 and terminal units 45 for rehabilitants 60. More specifically, the trainer systems 42 may be provided in facilities for rehabilitants 60 to perform training of their muscular forces, such as rehabilitation sites or sports gyms located in various places. The system server 41 functions as a data manager and storage server disposed in a management center or a computer center managed by a system manager or supervisor for the system 40. The terminal units 45 for rehabilitants 60 are provided in premises or work sites of rehabilitants 60 and are operable by the rehabilitants 60.

In the illustrative embodiment, the trainer systems 42 and the server 41 are interconnected for telecommunications over a telecommunications network, symbolically depicted with interconnections 47 in FIG. 1. The server 41 is also interconnected to the terminals 45 for rehabilitants for telecommunications over the network 47. The network 47 may be, e.g. the Internet. However, the network 47 may also include other types of networks, such as dedicated wired or wireless communication network, public communication network, on-line network, Intranet, LAN (Local Area Network), WAN (Wide Area Network) and other various sorts of transmission networks.

The manager or the supervisor of the system 40 may, for example, be a medical organization, such as hospital, or a business organization managing a sports gym. However, the manager or the supervisor may be any kinds of organization or individual. The rehabilitants, or trainees, 60 possibly have to conclude respective agreements for using the system 40 with the manager or the supervisor of the system 40. In the illustrative embodiment, there are three trainer systems 42 and two terminals 45 provided for the rehabilitants 60. However, the numbers of the trainer systems 42 and the terminals 45 for rehabilitants may be arbitrary and set in a desired manner. Moreover, the trainer systems 42 and the terminals 45 for rehabilitants may be provided at any optional locations and sites.

Those trainer systems 42 may be the same in structure as each other. Then, referring to FIG. 2, each of the systems 42 includes a trainer device 43 for measuring the rehabilitant or trainee 60 to obtain his or her living body data and for training him or her, and an operator terminal unit 44 serving as a menu formulator or scheduler for planning a rehabilitation training menu, or schedule. To the trainer device 43, applicable is, e.g. a bi-articular arm device proposed by JP patent laid-open publication No. 2007-61137 for measuring the force of muscles of, and for training, the rehabilitant 60. The operator terminal unit 44 may be implemented by, e.g. a personal computer, and include an input device, a display device, a processor unit, such as a central processor unit (CPU) or micro processor unit (MPU), a memory device, such as a magnetic disc or a semiconductor storage, and a communication interface. The input unit may be a manipulatable input device, such as keyboard, mouse or touch panel. The display device may, for example, be a cathode-ray tube (CRT) display, a liquid-crystal display or a light emitting diode (LED) display. The operator terminal 44 is interconnected to the trainer device 43 as symbolically depicted with interconnections 49 and ultimately to the server 41 for telecommunications and operative as an upper-order device with respect to the trainer device 43.

An operator working for facilities for training the force of muscles, such as a trainer, acts on the operator terminal unit 44 to acquire data of the force of muscles, as living body data, of the rehabilitant 60, which was measured by means of the trainer device 43. The operator may transmit, as required, the so acquired living body data to the server 41 for storage therein. The operator may also act on the operator terminal unit 44 to fetch living body data of the same rehabilitant 60 which have been kept in the server 41. The operator then operates the terminal 44 to compare the so fetched data to the currently acquired living body data of the rehabilitant 60 to calculate the differences therebetween, and he or she can thereby formulate a menu for rehabilitation suited for the rehabilitant 60 accordingly. The operator may also act on the operator terminal 44 to control the trainer device 43 so as to execute the operations for training the force of muscles in accordance with the menu for rehabilitation thus formulated.

The system server 41 may be implemented by a computer having, e.g. an operating unit, a storage unit, a manual input unit, a display unit and a communication interface. The operating unit may be a CPU or an MPU, while the storage may be a magnetic disc or a semiconductor memory device. The manual input unit may be a keyboard or a mouse, while the display unit may be a CRT or a liquid crystal display. The living body data of the rehabilitant 60 may be kept or registered for a time period stipulated under the agreement concluded with the rehabilitant 60. This time period may be extended by, e.g. updating the agreement. The living body data may be kept in the server 41 while being updated and/or supplemented periodically or non-periodically.

The terminal units 45 for rehabilitants may also be, implemented by, e.g. a personal computer including an input unit, a display unit, a processing unit, a storage device and a communication interface, by way of examples. The input unit may, for example, be a keyboard, a mouse or a touch panel, and the display unit may be a visual display device, such as a CRT, a liquid crystal display or an LED display. The storage device may be a magnetic disc or a semiconductor memory.

The rehabilitant 60 may word the terminal 45 to make an access to the server 41 in order to browse his or her own living body data.

Figure 3:
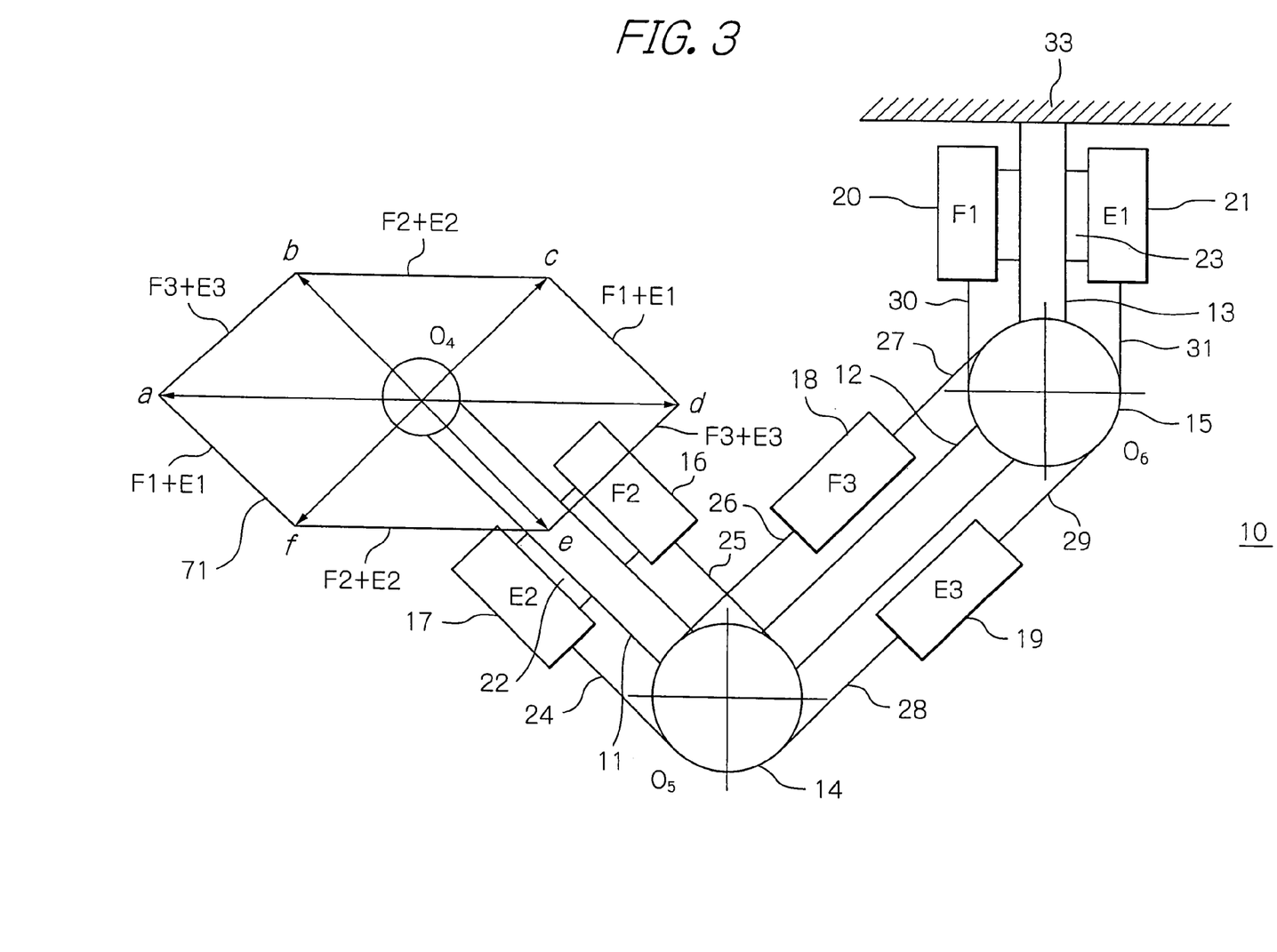
FIG. 3 schematically shows the constitution of a bi-articular arm device of the trainer device in the illustrative embodiment.
Figure 4:
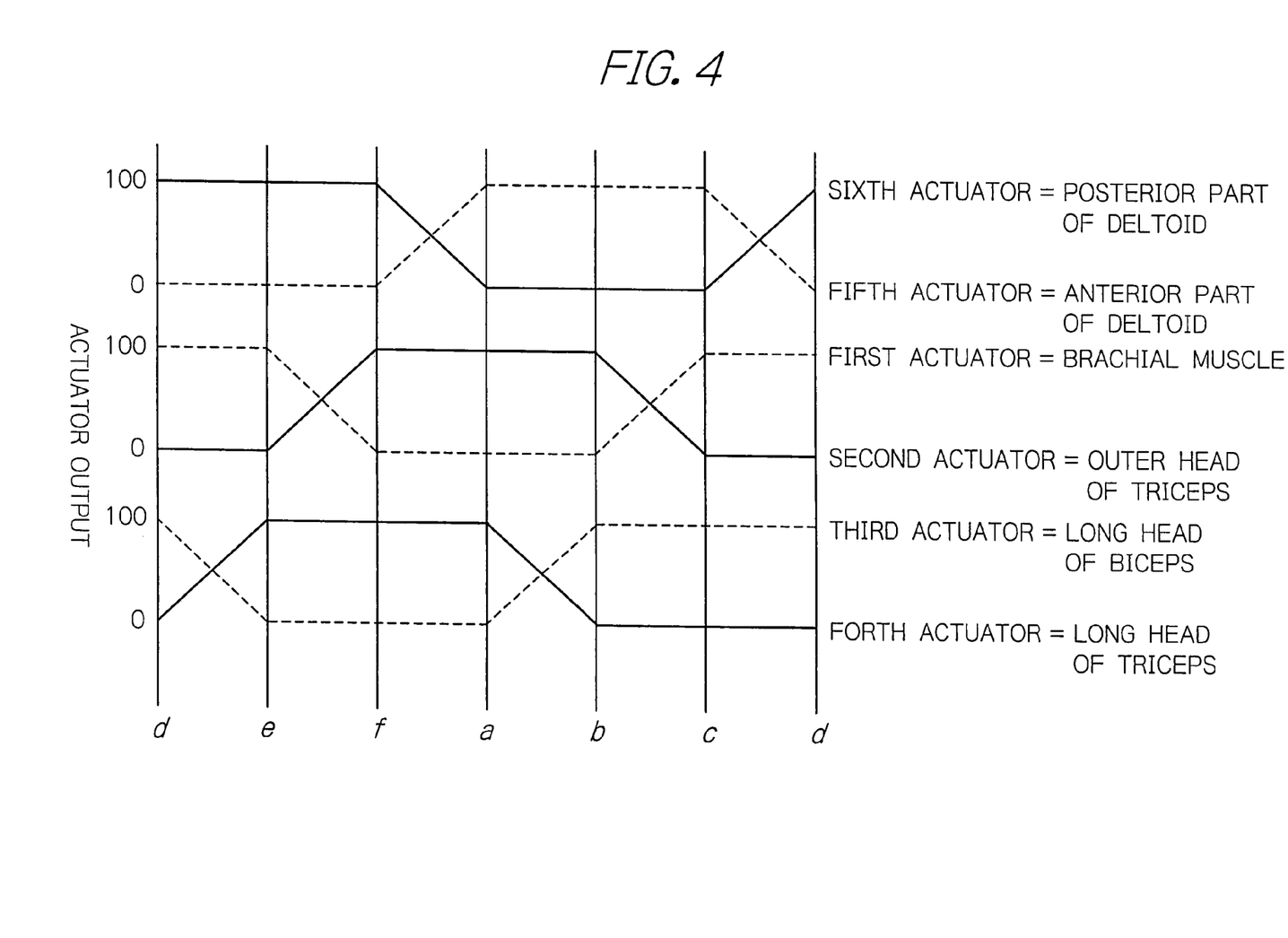
FIG. 4 is a diagrammatic view for use in describing the driving sequence of actuators and force directions in the illustrative embodiment.

The structure of the trainer device 43 will now be described in detail. FIG. 3 schematically shows the structure of a bi-articular arm device 10 of the trainer device 43 of the present embodiment, and FIG. 4 is a diagrammatic view for use in describing the driving sequence of actuators of the present embodiment and force directions.

In FIG. 3, the bi-articular arm device 10 is included in the trainer device 43 of the present embodiment and has a structure which simulates an upper limb, that is, an arm, of the human being. Although the bi-articular arm device 10 may be of a structure which simulates the lower limb, that is, a leg of the human being, the following description is directed to a case where the bi-articular arm device has the structure simulating the upper limb.

The bi-articular arm device 10 has a first link 11 and a second link 12 respectively corresponding to a lower arm and an upper arm. The arm device 10 also has a frame 13 serving as a base relating to the shoulder and having its root end, at the upper end in the figure, secured on a stationary member 33, which is in turn secured on the foundation of a building, not shown. On the foremost, or opposite, part of the frame 13, which is the lower end in the figure, there is rotatably mounted the root end of the second link 12 via a second joint section 15 which is for the shoulder joint. To the foremost part of the second link 12, is rotatably connected a root end of the first link 11 via a first joint section 14 which is for the elbow joint.

The arm device 10 also has first to sixth actuators 16 to 21. The arm device 10 further includes a first bracket 22 for securing the first actuator 16 and the second actuator 17 on the first link 11. The arm device 10 also includes a second bracket 23 for securing the fifth actuator 20 and the sixth actuator 21 on the frame 13.

In FIG. 3, the reference numerals 24 to 31 denote wires. The wire 24 connects the second actuator 17 to an elbow pulley, not shown, secured on the second link. The wire 25 connects the first actuator 16 to the elbow pulley, not shown, secured on the second link. The wire 26 connects the third actuator 18 to an elbow pulley, also not shown, secured on the first link. The wire 27 connects the third actuator 18 to a shoulder pulley, also not shown, secured on the frame. The wire 28 connects the fourth actuator 19 to the shoulder pulley fixed on the frame. The wire 29 connects the fourth actuator 19 to the shoulder pulley secured on the frame. The wire 30 connects the fifth actuator 20 to the shoulder pulley, also not shown, secured on the second link. The wire 31 connects the sixth actuator 21 to the shoulder pulley fixed on the second link.

The first actuator 16 and the second actuator 17 generate a driving force for rotating the first link 11, while the third actuator 18 and the fourth actuator 19 generate a driving force for rotating the second link 12 so that the first and second links rotate independently of each other. The fifth actuator 20 and the sixth actuator 21 generate the driving force for simultaneously rotating the first link 11 and the second link 12 with respect to the frame 13.

FIG. 3 depicts the directions a to f of the force generated at the distal end of the first link 11. For example, a force may be generated in a direction a in FIG. 3 by controlling the outputs of the first to sixth actuators 16 to 21, as indicated by a driving sequence a shown in FIG. 4. That is, the driving sequences a to f shown in FIG. 4 correspond to the force generating directions a to f in FIG. 3. It is noted that FIG. 4 also shows how each of the first to sixth actuators 16-21 correspond to different one of the muscles of the upper limb, as will be described later.

It is known that, if outputs of the first actuator 16, second actuator 17, third actuator 18, fourth actuator 19, fifth actuator 20 and sixth actuator 21 are denoted by F2, E2, F3, E3, F1 and E1, respectively, then the generated magnitudes of the force a to f in case of driving the actuators in accordance with the driving sequence shown in FIG. 4 will form a hexagon 71 shown in FIG. 3.

It is also known that line segments ab and de are each equal in length to the sum of the magnitudes of the force F3 and E3, line segments bc and ef are each equal in length to the sum of the magnitudes of the force F2 and E2, and the line segments cd and af are each equal in length to the sum of the magnitudes of the force F1 and E1.

Figure 5:
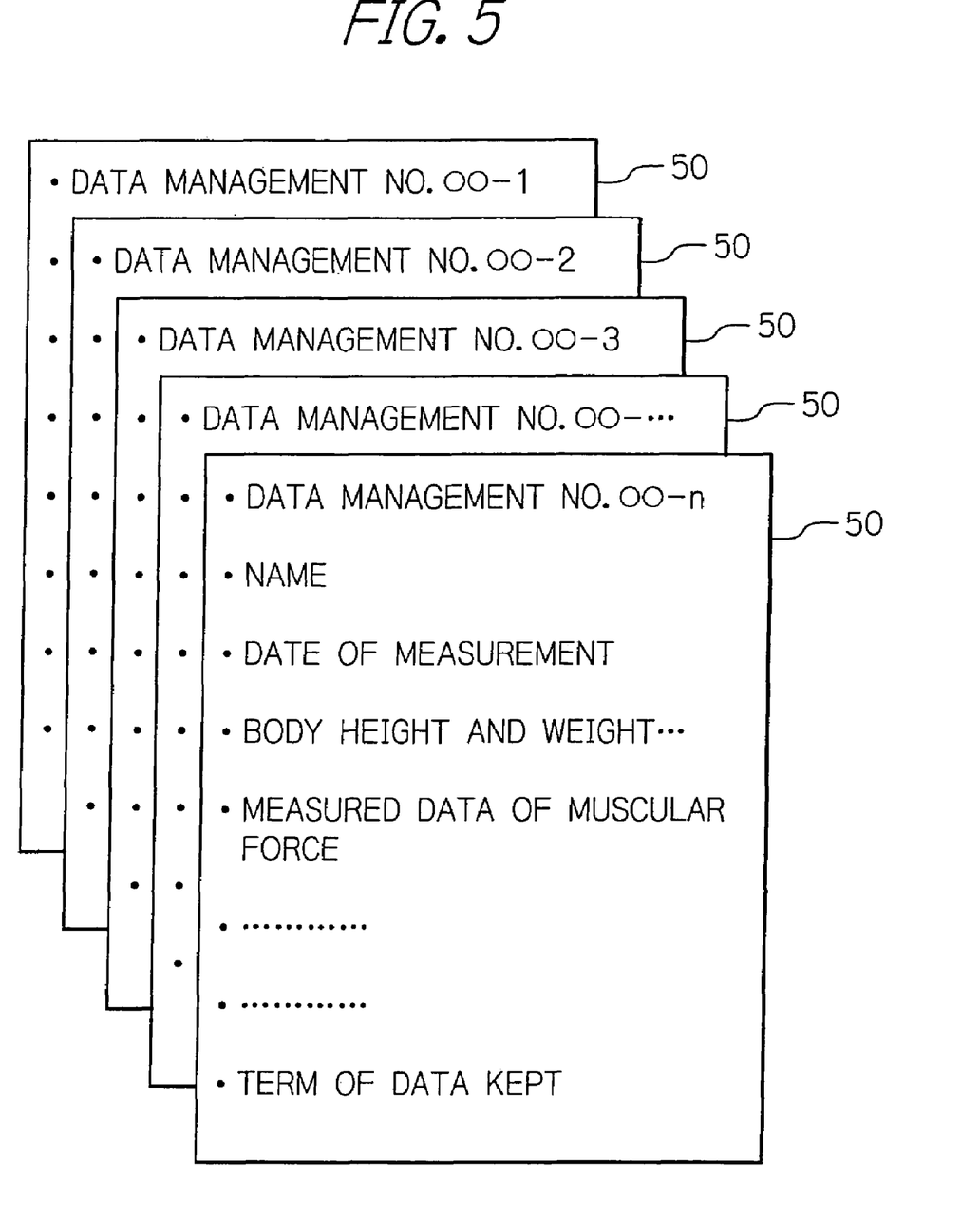
FIG. 5 is a diagrammatic view showing living body data stored in a server in the illustrative embodiment.

The operation of the system 40 of the above structure will now be described in detail. FIG. 5 exemplarily shows living data kept in the server in the embodiment of the present invention. Initially, a person wishing to get rehabilitation, i.e. possible rehabilitant, 60 concludes an agreement for using the system 40 in facilities provided with the trainer systems 42, such as a rehabilitation center or sports gym. It is noted that the agreement may be concluded at a location different from the facilities provided with the trainer systems 42, such as an agent's office.

On conclusion of the agreement, the possible rehabilitant 60 uses the trainer device 43 in the trainer system 42 to measure the force of his or her own muscles at the time of, e.g. the conclusion of the agreement. Data of the force of muscles, measured by the trainer device 43, are transmitted from the operator terminal 44 to the server 41 for storage therein as living body data of the possible rehabilitant 60. The living body data preferably include basic data such as body height or body weight. The living body data are kept in the server 41 for the stipulated time period in a form shown in FIG. 5. In this figure, the data format includes data files 50 kept in the server 41. In those data files 50, living body data of a plural number of rehabilitants or possible rehabilitants 60 are saved in connection with data management numbers, personal names and dates of data measurement.

When the possible rehabilitant 60 has concluded the agreement in the facilities provided with the trainer system 42, the trainer system 42 of the facilities where the agreement was concluded is used to measure his or her living body data and register the data therein. In case the possible rehabilitant 60 has concluded the agreement in an agent's office not provided with the trainer system 42, the trainer system 42 of the facilities specified by the agent may be used to measure his or her living body data and registered the data.

The possible rehabilitant 60 may browse his or her living body data by accessing the server 41 on the terminal 45. The possible rehabilitant 60 may use the trainer system 42 of the facilities specified by the agreement, periodically or non-periodically, to measure living body data, to register the so measured additional living body data. Meanwhile, the registered living body data, inclusive of the additionally registered data, are saved in the server 41 during the time stipulated by the agreement.

Subsequently, it is possible for the possible rehabilitant 60 to have his or her force of muscles degraded as he or she gets older, to have his or her body impaired by an accident or disease, or to accept medical care for prolonged time due to a physical injury or disease so that it becomes necessary for him or her to take the course of rehabilitation. In such a case, the possible rehabilitant 60 may use the trainer system 42, provided in facilities, such as a rehabilitation center or a sports gym, as stipulated by the agreement, to take the course of rehabilitation.

In this case, the possible rehabilitant, now actual rehabilitant, 60 again measures the force of muscles, on the trainer device 43, to newly acquire the living body data just prior to taking the course of rehabilitation. The living data are then transmitted to the operator terminal 44. The operator terminal 44 accesses the server 41 to retrieve and acquire the living body data of the rehabilitant 60 registered and kept in the server 41. The living body data acquired from the server 41, that is, the data before the time rehabilitation has become necessary for the rehabilitant 60, as well as the newly measured living body data, that is, the data measured when the rehabilitation has become necessary for the rehabilitant 60, are compared with each other to prepare a menu for rehabilitation based on the difference between the two data.

The rehabilitant 60 then uses the trainer device 43, in accordance with the so prepared menu for rehabilitation, to train the muscle which has become weaker, that is, the muscle in need of training.

The method for measuring the force of muscles of the rehabilitant 60, with the use of the bi-articular arm device 10, will now be described in detail. FIG. 6 will be referenced for describing a method for measuring the force of muscles of the rehabilitant, using the aforementioned bi-articular arm device 10.

Figure 6:
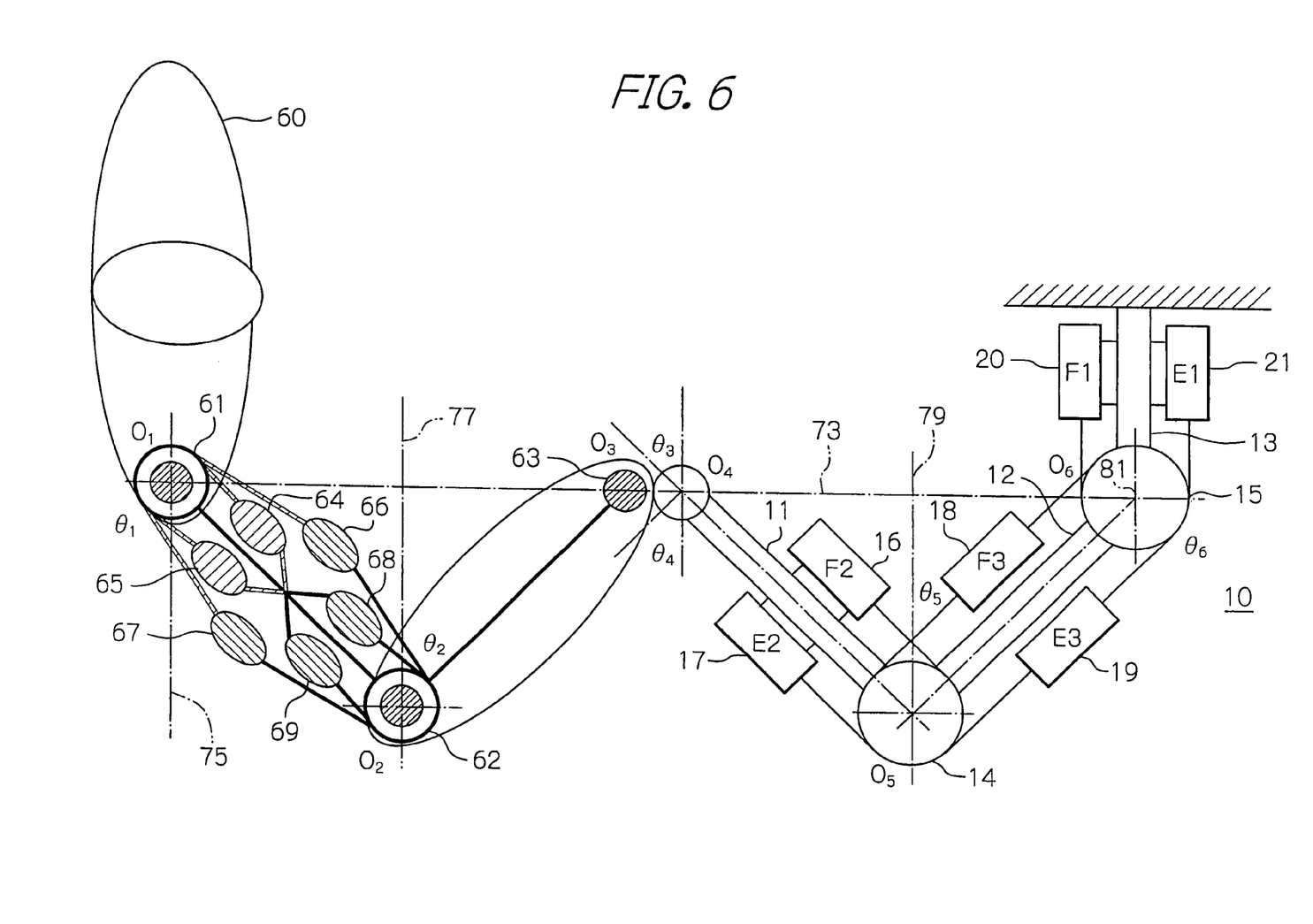
FIG. 6 is a schematic view for use in illustrating a method for measuring the force of muscles of a rehabilitant using a bi-articular arm device of the trainer device in the illustrative embodiment.

In FIG. 6, the reference numeral 61 denotes a shoulder joint interconnecting the upper body and an upper arm of the rehabilitant 60. The reference numeral 62 denotes an elbow joint interconnecting the upper and lower arms of the rehabilitant 60, and the reference numeral 63 denotes a wrist joint interconnecting the lower arm and the corresponding hand of the rehabilitant 60. The wrist joint is the distal end of the upper limb.

The reference numerals 64 to 69 denote muscles in the upper limb of the rehabilitant 60. Specifically, the reference numeral 64 denotes the anterior part of the deltoid, the reference numeral 65 denotes the posterior part of the deltoid, and the reference numeral 66 denotes a caput longum (long head) of the biceps of the upper arm. The reference numeral 67 denotes a caput longum (long head) of the triceps of the upper arm, the reference numeral 68 denotes a brachial muscle, and the reference numeral 69 denotes an caput lateralis (outer head) of the triceps of the upper arm. A center point of the shoulder joint 61 is denoted by $O_1$, a center point of the elbow joint 62 is denoted by $O_2$ and a center point of the wrist joint 63 is denoted by $O_3$. In the bi-articular arm device 10, a center point of a circular part at the distal end of the first link 11 is denoted by $O_4$, a center point of the first joint section 14 is denoted by $O_5$ and a center point of the second joint section 15 is denoted by $O_6$.

When measuring the force of muscles of the rehabilitant 60, the positional relationships between the bi-articular arm device 10 and the rehabilitant 60 are set as illustrated in the figure. More specifically, the center points $O_1$, $O_3$, $O_4$ and $O_6$ are made to reside on the common straight line 73. With an angle $\theta_1$ between a line segment $O_1O_2$ and a line 75 drawn vertically from the center point $O_1$, an angle $\theta_2$ between a line segment $O_2O_3$ and a line 77 drawn vertically from the center point $O_2$, an angle $\theta_5$ between a line segment $O_5O_6$ and a line 79 extending vertically from the center point $O_5$, and with an angle $\theta_6$ between the line segment $O_5O_6$ and a line 81 drawn vertically from a center point $O_6$, these angles may be set so that $\theta_1 = \theta_2 = \theta_5 = \theta_6 = \theta_{ref}$, where $\theta_{ref}$ is a value of angle optionally predetermined.

Initially, the rehabilitant 60 faces the bi-articular arm device 10, with the positional relationship between the bi-articular arm device 10 and the rehabilitant 60 taken as schematically depicted in FIG. 6. With this positional relationship taken as the initial position, count values of an encoder, not shown, adapted for measuring the angles of rotation of the first link 11 with respect to the second link 12 and of the frame 13 with respect to the second link 12, are recorded. It is to be noted that the wrist joint 63 of the rehabilitant 60 is secured on the distal end of the first link 11 by appropriate means. For example, the wrist joint 63 of the rehabilitant 60 may be fastened by a string or fastener to the distal end of the first link 11 to secure the wrist joint 63 on the distal end of the first link 11. Alternatively, the rehabilitant 60 may grip the distal end of the first link 11 to immobilize the wrist joint 63 to the distal end of the first link 11. It is also noted that the rehabilitant 60 is instructed at the outset so that he or she will, when subjected to a force acting from the bi-articular arm device 10, exert a force from his or her upper limb against the force applied so that the position of his or her wrist joint 63 will not be moved from the initial position shown in FIG. 6.

The bi-articular arm device 10 then generates a force acting in the direction a shown in FIG. 3 at the distal end of the first link 11. In this case, the force is generated in the direction a, by controlling the outputs of the first actuator 16 to the sixth actuator 21, as indicated by the driving sequence a shown in FIG. 4. Specifically, the outputs at the first actuator 16, third actuator 18 and sixth actuator 21 are fixed at zero, and the outputs of the second actuator 17, fourth actuator 19 and fifth actuator 20 are varied simultaneously in equal amounts, that is, progressively increased in synchronism from the zero value. By so doing, the force generated at the distal end of the first link 11 of the bi-articular arm device 10 for acting in a direction a is increased progressively.

On the other hand, the rehabilitant 60 generates, in accordance with advance instructions, the force for causing movement of his or her wrist joint 63 in the direction opposite to the direction a, that is, in the direction d, and exerts a force in his or her upper limb to prevent the position of his or her wrist joint 63 from moving from the initial position. Since the force generated by the distal end of the first link 11 in the direction a is increased progressively, the force the rehabilitant 60 exerts in his or her upper limb is also increased progressively, to prevent movement of the position of his or her wrist joint 63 secured on the distal end of the first link 11.

The bi-articular arm device 10 checks for deviation from an initial position of the distal end of the first link 11, based on a count value of the encoder, at the same time as the arm device increases the outputs of the second actuator 17, fourth actuator 19 and fifth actuator 20 in synchronization with one another.

The rehabilitant 60 exerts the force in his or her upper limb to prohibit movement of the position of his or her wrist joint 63, as described above. Thus, as long as the force exerted by the rehabilitant 60 in his or her upper limb is substantially in equilibrium with the force generated by the bi-articular arm device 10, the position of the distal end of the first link 11 secured to the wrist joint 63 is not moved from its initial position. However, if the force generated by the bi-articular arm device 10 is increased and exceeds the limit of the force the rehabilitant 60 exerts in his or her upper limb, that is, the maximum force that may be exerted by the rehabilitant 60, the force generated by the bi-articular arm device 10 overcomes the force exerted by the rehabilitant 60 in his or her upper arm. Hence, the distal end of the first link 11 is moved in the direction a. Consequently, the force generated by the bi-articular arm device 10 at a time point when the distal end of the first link 11 commences to be moved in the direction a may be thought of as being the maximum value of the force exerted by the rehabilitant 60 for causing movement of his or her wrist joint 63 in the direction d, that is, the maximum value of the force of muscles of the upper limb of the rehabilitant 60.

Thus, in the present embodiment, if it is verified that, based on the count value of the encoder, the position of the distal end of the first link 11 has been moved from its initial position in the direction a, the values of the output E2 of the second actuator 17, the output E3 of the fourth actuator 19 and the output F1 of the fifth actuator 20 at the time point of movement in the direction a of the distal end of the first link 11 from the initial position are recorded. The so recorded values of the second actuator 17, fourth actuator 19 and fifth actuator 20 represent output values corresponding to the maximum value of the force of muscles of the upper limb developed by the rehabilitant 60 to cause movement of his or her wrist joint 63 in the direction d. Thus, it is possible to record output values of the respective actuators of the bi-articular arm device 10 corresponding to the maximum value of the force of muscles of the upper limb of the rehabilitant 60 he or she is able to develop to cause movement of his or her wrist joint 63 in the direction d.

The bi-articular arm device 10 then repeats the above operation to generate the magnitudes of the force in the directions b to f at the distal end of the first link 11. The bi-articular arm device records output values of the respective actuators of the bi-articular arm device 10 corresponding to the maximum values of the force of muscles of the upper limb developed by the rehabilitant 60 to cause movement of the wrist joint 63 in the directions e to c. The sequence of directions in which the force is to be generated by the bi-articular arm device 10 is not limited to the direction a to f and may be changed as necessary.

If the force generated in the direction a at the distal end of the first link 11 by the bi-articular arm device 10 is denoted as actuator output Fa, the actuator output Fa may be calculated in accordance with the following expression (1):

$$Fa = E2 + F1 \times \sin \theta_{ref} + E3 \times \sin \theta_{ref} \quad (1)$$

where the unit of Fa is %.

In a similar manner, the magnitudes of the force generated by the bi-articular arm device 10 at the distal end of the first link 11 in the directions b to f may be found as actuator outputs Fb to Ff. Based on the result, it is possible to draw a hexagon 71 shown in FIG. 3.

The method for calculating the magnitudes of the force of muscles of the rehabilitant 60 based on the recorded output values of the actuators of the bi-articular arm device 10 will now be described in detail.

The muscular force of the anterior part of the deltoid 64 in the upper limb of the rehabilitant 60 is denoted by f1, the muscular force of the posterior part of the deltoid 65 is denoted by e1, the muscular force of the caput longum (long head) of the biceps of the upper arm 67 is denoted by e3, the muscular force of the brachial muscle 68 is denoted by f2 and the muscular force of the caput lateralis (outer head) of the triceps 69 of the upper arm is denoted by e2. The relationship between the output values of the respective actuators of the bi-articular arm device 10 and the magnitudes of the force of the respective muscles of the upper limb of the rehabilitant 60 may be represented by the following expressions (2) to (4):

$$F2 + E2 = f2 + e2 \quad (2)$$

$$F3 + E3 = f3 + e3 \quad (3)$$

$$F1 + E1 = f1 + e1 \quad (4)$$

Thus, the maximum values of the force of the muscles of the upper limb of the rehabilitant 60 may be calculated by substituting the recorded output values of the respective actuators of the bi-articular arm device 10 in the above expressions (2) to (4).

Specifically, the bi-articular arm device 10 has a structure which simulates the upper limb of the human being, and includes actuators relating to groups of antagonistic mono-articular muscles and antagonistic bi-articular muscles of the upper limb. More specifically, the bi-articular arm device includes actuators relating to the anterior part of the deltoid 64, posterior part of the deltoid 65, caput longum (long head) of the biceps of the upper arm 66, caput longum (long head) of the triceps of the upper arm 67, brachial muscle 68 and caput lateralis (outer head) of the triceps 69 of the upper arm. Hence, by securing the wrist joint 63 of the rehabilitant 60 to the distal end of the first link 11, so that, if the rehabilitant 60 is subjected to the force applied from the bi-articular arm device 10, the wrist joint 63 is not moved from the initial position, it is possible to measure outputs of respective muscles of the group of antagonistic mono-articular joint muscles and the group of antagonistic bi-articular joint muscles, that is, the force of muscles, of the upper limb of the rehabilitant 60. That is, by having the force in the six directions at the distal end of the first link 11 oppose to the force of the rehabilitant 60, it becomes possible to measure the magnitudes of the force in the six directions developed at the distal end of the upper limb of the rehabilitant 60. In this case, it is possible to measure the force of muscles for causing movement of the wrist joint 63 in the six directions by varying the directions of the force generated at the distal end of the first link 11 in six different directions.

Since the rehabilitant 60 need not be conscious of the output direction, the force of muscles of the rehabilitant 60 may be measured easily accurately without imposing excess load on the rehabilitant 60.

The method of training the force of muscles of the rehabilitant 60 will now be described. FIG. 7 shows exemplary results of measurement of the force of muscles of the rehabilitant 60 in the embodiment of the present invention.

It is assumed that measurement of the force of muscles of the upper limb of the rehabilitant, specifically, the anterior part of the deltoid 64, posterior part of the deltoid 65, caput longum (long head) of the biceps of the upper arm 66, caput longum (long head) of the triceps of the upper arm 67, brachial muscle 68 and caput lateralis (outer head) of the triceps of the upper arm 69, has been finished. If, as a result of the measurement, the force of certain muscles is found to be weak, as shown in the figure, the force of the muscles in question needs to be improved by training. It is noted that, in FIG. 7, a broken line hexagon 51 denotes the force of muscles of the rehabilitant 60 measured before rehabilitation becomes necessary, and a solid line hexagon 52 denotes the force of the same muscles measured when rehabilitation has become necessary. The example shown in FIG. 7 is directed to the case where the force of muscles of the long head of the biceps of the upper arm 66 has become considerably weaker.

In this case, the force of muscles of the rehabilitant 60 can be trained using the bi-articular arm device 10. If the results of measurement of the force of muscles behave as shown in FIG. 7, the output of the long head of the biceps of the upper arm 66 is weaker. Hence, it is effective that the load applied in the course of training to the long head of the biceps of the upper arm 66 is made higher than the load applied to other muscles. In this case, training of the force of muscles of the rehabilitant 60 may be appropriate if the training menu for improving the output of the muscular force of the long head of the biceps of the upper arm 66 is carried out.

In the case of training the force of muscles of the rehabilitant 60, using the bi-articular arm device 10, he or she faces the bi-articular arm device 10, as shown in FIG. 6, like in the case of measuring the force of muscles. The wrist joint 63 of the rehabilitant 60 is secured by suitable optional means to the distal end of the first link 11. It is noted that the rehabilitant 60 is instructed at the outset so that he or she will, when subjected to a force acting from the bi-articular arm device 10, exert a force from his or her upper limb against the force applied so that the position of his or her wrist joint 63 will not be moved from the initial position, that is, the position shown in FIG. 6.

In general, concerted activities of the muscles of the same pattern as the pattern shown in FIG. 4 are taking place in the upper limb of the human being. It is noted that FIG. 4 shows the correspondence between the respective actuators of the bi-articular arm device 10 and the respective muscles of the upper limb of the human being. The directions of force generated in case the force of muscles of the upper limb of the human body are developed in accordance with the driving sequences a to f shown in FIG. 4 are indicated by the directions a to f in FIG. 7. The directions a to f shown in FIG. 7 are represented when looking from the rehabilitant 60. These directions are symmetrical with respect to the directions a to f when looking from the bi-articular arm device 10 shown in FIG. 3.

Figure 7:
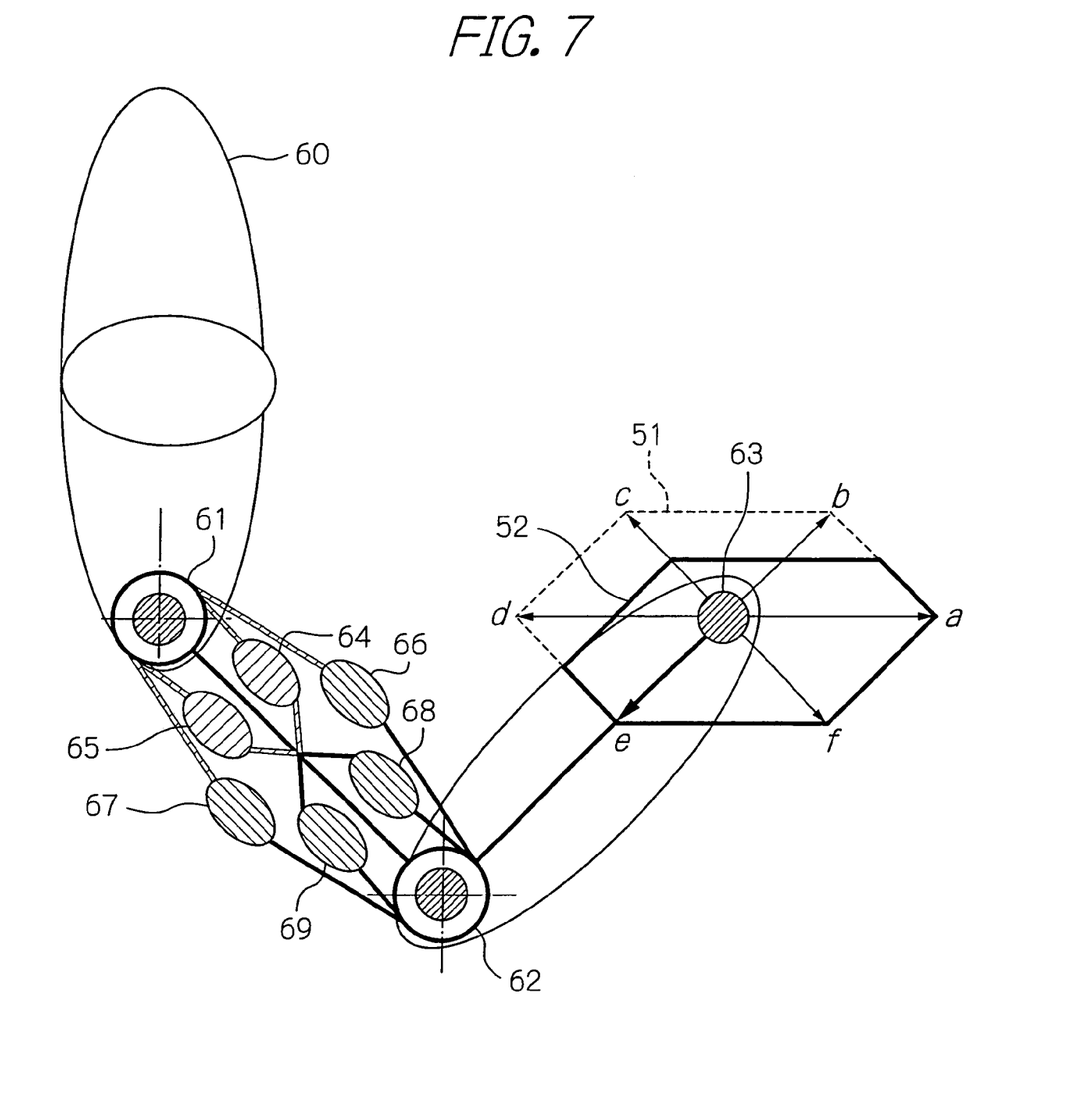
FIG. 7 is a diagrammatic view for use in describing measured results of the force of muscles of the rehabilitant in the illustrative embodiment.

Thus, if the distal end of the first link 11 of the bi-articular arm device 10 has generated the force in the direction b shown in FIG. 3, and the rehabilitant 60 has exerted the force in his or her upper limb to make the position of his or her wrist joint 63 unmovable, he or she generates the force for causing movement of his or her wrist joint 63 in the direction b shown in FIG. 7. Specifically, such a load which will cause movement of the wrist joint 63 in the direction b shown in FIG. 7 is applied to the respective muscles of the upper limb of the rehabilitant 60. In this case, the anterior part of the deltoid 64, the outer head of the triceps of the upper arm 69 and the long head of the biceps of the upper arm 66 are placed under a load, so that the force of muscles is generated therein, as indicated by the driving sequence b shown in FIG. 4.

If such a load which will cause movement of the wrist joint 63 in the direction d shown in FIG. 7 is applied to the upper limb of the rehabilitant 60, then the posterior part of the deltoid 65, the brachial muscle 68 and the long head of the biceps of the upper arm 66 are placed under a load. Hence, the force of muscles is developed in these muscles, as indicated by the driving sequence d shown in FIG. 4.

If such loads which will cause movements of the wrist joint 63 in the directions b and d shown in FIG. 7 are applied at a ratio of 1:1 to the upper limb of the rehabilitant 60, then even loads are applied to the mono-articular muscles, that is, to the anterior part of the deltoid 64, the posterior part of the deltoid 65 and the brachial muscle 68. A load twice as high as applied to the mono-articular muscles is applied to the long head of the biceps of the upper arm 66, while no load is applied to the long head of the triceps of the upper arm 67. Thus, in such a case, a high load is selectively applied to the long head of the biceps of the upper arm 66, while a low load is selectively applied to the long head of the triceps of the upper arm 67.

Meanwhile, the magnitude of the load applied to the upper limb of the rehabilitant 60 is controlled based on the result of measurement of the force of muscles. In this case, the outputs of the respective actuators of the bi-articular arm device 10 may be controlled so as to apply to each muscle the load proportionate to the measured output of each muscle in order to continue to apply an optimum load to each muscle.

In this manner, an optimum load may selectively be applied to each muscle in the upper limb of the rehabilitant 60 to render it possible to carry out effective training without imposing excess load on the rehabilitant 60. Hence, the force of muscles of the rehabilitant 60 may effectively be improved in a well-balanced fashion.

If the rehabilitant 60 is desirous to improve his or her force of muscles further from the current state, the target force of the muscles is set from the measured results of the magnitudes of the force of the respective muscles of the rehabilitant 60. Training is carried out with this target force of muscles as a target. In this case, training is repeated as the outputs of the first actuator 16 to the sixth actuator 21, relating to the driving sequences a to f shown in FIG. 4, are progressively increased from the current values of the magnitudes of the force of respective muscles of the rehabilitant 60. By doing so, it is possible to improve the force of muscles of the entire upper limb of the rehabilitant 60 in a well-balanced fashion.

The bi-articular arm device 10 has its structure comparable to the upper limb of the human being, and has its actuators related with the muscles of the group of the antagonistic mono-articular muscles and with those of the group of the antagonistic bi-articular muscles. These muscles are the anterior part of the deltoid 64, the posterior part of the deltoid 65, the long head of the biceps of the upper arm 66, the long head of the triceps of the upper arm 67, the brachial muscle 68 and the outer head of the triceps of the upper arm 69. Thus, the wrist joint 63 of the rehabilitant 60 is secured to the distal end of the first link 11. If the force is applied from the bi-articular arm device 10 to the rehabilitant 60, then he or she may exert the force so that the position of his or her wrist joint 63 will not be moved from an initial position. In this case, load may be applied selectively to the muscles of the group of the antagonistic mono-articular muscles and to those of the group of the antagonistic bi-articular muscles, in the upper limb of the rehabilitant 60, to render it possible to carry out effective training. In such a case, it is possible for the bi-articular arm device 10 to select the direction of the force generated at the distal end of the bi-articular arm device 10 to select the muscle to be loaded for training.

The force of muscles of the rehabilitant 60 may be trained with the use of the bi-articular arm device 10, used for measuring the muscular force. In other words, there is no necessity of providing separate devices for measuring the force of muscles and for training, thus reducing the equipment expenses.

Moreover, since the bi-articular arm device 10 has its structure which simulates the upper limb of the human body, the rehabilitant 60 is able to proceed to training without extraneous feeling.

In the present embodiment, living body data of the rehabilitant 60 before he or she is in need of rehabilitation are measured, and the so measured living body data are kept in the system. When the rehabilitant 60 is in need of rehabilitation, the living body data before he or she is in need of rehabilitation are compared to the living body data when the rehabilitant 60 is in need of rehabilitation. The muscle which has become weaker may then be specified and trained. The goal of training may then be optimized for the rehabilitant 60 so that it may be expected to improve the effect of rehabilitation.

In the illustrative embodiment, the description has been proceeded to in respect of the living body data of the rehabilitant 60 being measured by means of one and the same trainer device 43 which was also used by the same person 60 when he or she was not impaired. It is however not necessary to use, when rehabilitation is get required for the rehabilitant 60, one and the same trainer device 43 which he or she used when not impaired, but the same or similar kind of trainer device may be applicable so far as his or her living body data are recorded in the system server 41 or any other data storage sites. If a different kind or type of trainer device is used instead of the trainer device 43, then the system server 41 or any other data storage sites may preferably include a converter, such as a conversion table and/or program sequence, which functions as converting living body data between different kinds or types of trainer devices such as device 43.

The entire disclosure of Japanese patent application No. 2006-224240 filed on Aug. 21, 2006, including the specification, claims, accompanying drawings and abstract of the disclosure is incorporated herein by reference in its entirety.

While the present invention has been described with reference to the particular illustrative embodiment, it is not to be restricted by the embodiment. It is to be appreciated that those skilled in the art can change or modify the embodiment without departing from the scope and spirit of the present invention.

What is claimed is:

1. A system for rehabilitation training comprising:
   a trainer device for measuring living data of a person and for training the person;
   a data server for storing living body data of the person measured by said trainer device; and
   a menu formulator for forming a menu for rehabilitation of the person,
   said trainer device including a bi-articular arm device having a structure simulating an upper limb or a lower limb of a human being,
   said bi-articular arm device comprising at least one link on which the upper limb or lower limb of the human being is secured when the trainer device is used, and multiple actuators for generating a driving force for rotating said at least one link,
   said menu formulator comparing the living body data measured of the person, when undergoing a process of rehabilitation, by said trainer device to the living body data which was measured of the person, when not impaired, and is stored in said data server, to find out a difference between both of the living body data, thereby forming the menu based on the difference,
   said bi-articular arm device having the actuators generating forces at the distal end of said at least one link in multiple directions.

2. The system in accordance with claim 1, wherein the living body data is of force of a muscle, said menu formulator forming the menu with the muscle of which muscular force is weakened specified.

3. The system in accordance with claim 1, wherein said bi-articular arm device measuring muscular force of the upper limb or the lower limb of the person.

4. A system for rehabilitation training comprising:
   trainer means for measuring living data of a person and for training the person;
   data keeping means for keeping living body data of the person measured by said trainer means; and
   menu forming means for forming a menu for rehabilitation of the person,
   said trainer device including a bi-articular arm device having a structure simulating an upper limb or a lower limb of a human being,
   said bi-articular arm device comprising at least one link on which the upper limb or lower limb of the human being is secured when the trainer device is used, and multiple actuators for generating a driving force for rotating said at least one link,
   said menu forming means comparing the living body data measured of the person, when undergoing a process of rehabilitation, by said trainer means with the living body data which was measured of the person, when not impaired, and is stored in said data keeping means, to find out a difference between both of the living body data, thereby forming the menu based on the difference,
   said bi-articular arm device having the actuators generating forces at the distal end of said at least one link in multiple directions.

5. The system in accordance with claim 1, wherein the bi-articular arm device comprises a first link and a second link respectively corresponding to a lower arm and an upper arm, where a root end of the second link is rotatably connected to a base and a root end of the first link is rotatably connected to the foremost part of the second link and
   wherein the multiple actuators include a first group of actuators for generating the driving force for rotating the second link and first link independently of each other, and a second group of actuators for generating the driving force for simultaneously rotating the first link and second link with respect to the base.

6. The system in accordance with claim 4, wherein the bi-articular arm device comprises a first link and a second link respectively corresponding to a lower arm and an upper arm, where a root end of the second link is rotatably connected to a base and a root end of the first link is rotatably connected to the foremost part of the second link and
   wherein the multiple actuators include a first group of actuators for generating the driving force for rotating the second link and first link independently of each other, and a second group of actuators for generating the driving force for simultaneously rotating the first link and second link with respect to the base.

* * * * *